United States Patent
Margel et al.

(10) Patent No.: US 8,003,079 B2
(45) Date of Patent: Aug. 23, 2011

(54) CORE AND CORE-SHELL NANOPARTICLES CONTAINING IODINE FOR X-RAY IMAGING

(75) Inventors: Shlomo Margel, Rehovot (IL); Anna Galperin, Kfar Saba (IL)

(73) Assignee: Bar-Ilan University, Ramat-Gan (IL)

( * ) Notice: Subject to any disclaimer, the term of this patent is extended or adjusted under 35 U.S.C. 154(b) by 322 days.

(21) Appl. No.: 11/887,762

(22) PCT Filed: Apr. 4, 2006

(86) PCT No.: PCT/IL2006/000429
§ 371 (c)(1),
(2), (4) Date: Sep. 2, 2009

(87) PCT Pub. No.: WO2006/106513
PCT Pub. Date: Oct. 12, 2006

(65) Prior Publication Data
US 2009/0311192 A1    Dec. 17, 2009

(30) Foreign Application Priority Data

Apr. 5, 2005    (IL) .......................... 167861

(51) Int. Cl.
*A61K 49/04*    (2006.01)
*C08F 20/18*    (2006.01)
*C08F 20/56*    (2006.01)
*C08F 24/00*    (2006.01)
*C08F 251/00*    (2006.01)

(52) U.S. Cl. ................. 424/9.4; 526/292.1; 526/292.95; 526/292.5; 526/273; 526/303.1; 527/201; 527/314; 977/773; 977/928

(58) Field of Classification Search .................. 424/9.4; 526/292.1, 292.95, 292.5, 273, 303.1; 527/201, 527/314; 977/773, 928
See application file for complete search history.

(56) References Cited

U.S. PATENT DOCUMENTS

| | | | |
|---|---|---|---|
| 4,826,689 A | 5/1989 | Violanto et al. | |
| 5,019,370 A | 5/1991 | Jay et al. | |
| 5,160,725 A | 11/1992 | Pilgrimm | |
| 5,451,393 A | 9/1995 | Liversidge et al. | |
| 5,565,215 A | 10/1996 | Gref et al. | |
| 6,103,379 A * | 8/2000 | Margel et al. ................. | 428/403 |

FOREIGN PATENT DOCUMENTS

| | | |
|---|---|---|
| EP | 300828 | 1/1989 |
| WO | 89/00988 | 2/1989 |

OTHER PUBLICATIONS

A. Jayakrishnan et al., Biomedical Materials Research, vol. 24, p. 993, 1990.
N. Okamura et al., Molecular Structure, vol. 17, pp. 602-603, 2002.
K. Saralidze et al., Biomacromolecules, vol. 4, p. 793, 2003.

* cited by examiner

*Primary Examiner* — Michael M Bernshteyn
(74) *Attorney, Agent, or Firm* — Nixon & Vanderhye P.C.

(57) ABSTRACT

Nanoparticles having an average particle size of less than 2000 nm, wherein said nanoparticles comprise a polymer having pendant cleavable iodine substituted groups are provided. Processes for preparing the nanoparticles and their use as a contrast agent for X-ray imaging are also described.

33 Claims, 2 Drawing Sheets

CORE AND CORE-SHELL NANOPARTICLES CONTAINING IODINE FOR X-RAY IMAGING

Figure 1:
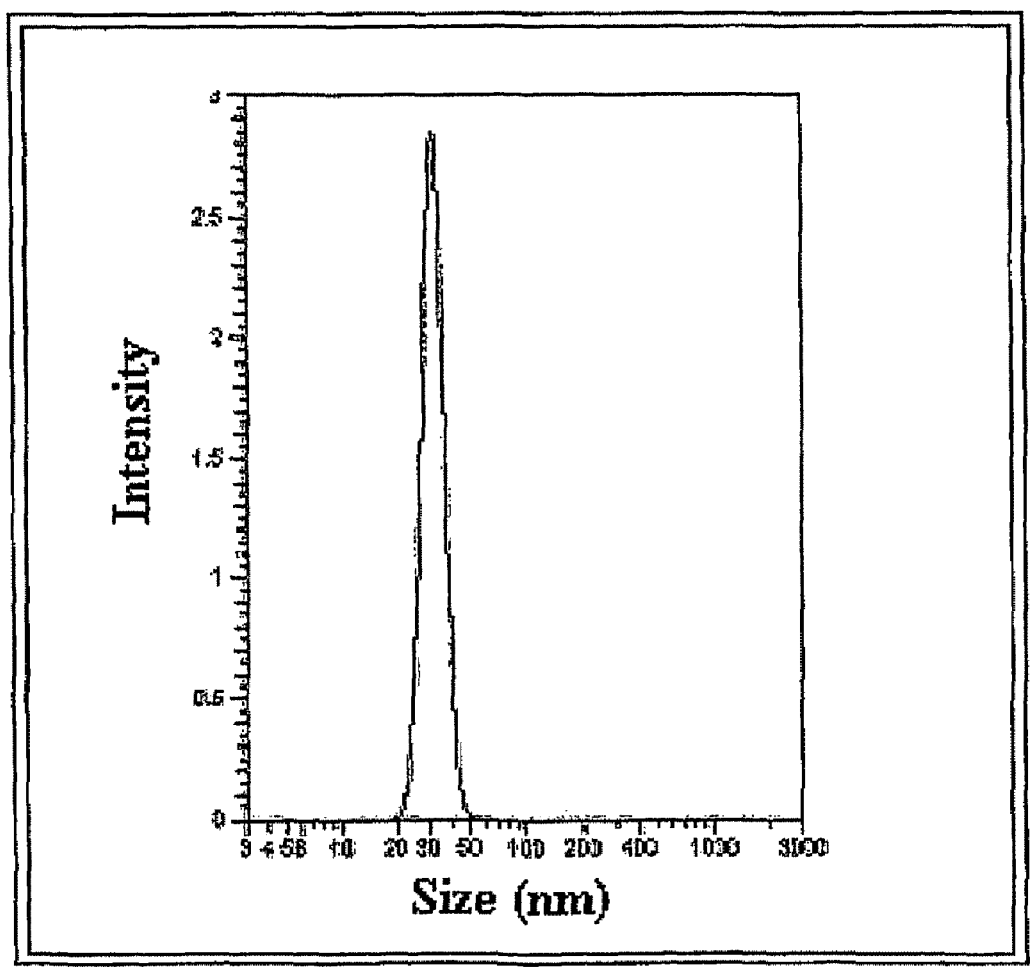

This application is the U.S. national phase of International Application No. PCT/IL2006/000429 filed 4 Apr. 2006 which designated the U.S. and claims priority to 167861 filed 5 Apr. 2005, the entire contents of each of which are hereby incorporated by reference.

X-ray imaging is a well known tool used for the detection and diagnosis of various disease states in the human body. The technique involves X-ray irradiation of the human body to produce a radiograph to be studied by a radiologist. It is of course well known to improve the visibility of the organs, blood vessels, or tissues under study using contrast agents that are administered to the patient before the irradiation process. It should be noted, however, that X-ray contrast agents may be used not only for medical imaging, but also for other applications, e.g. high refractive index materials and detection of various materials such as plastics, inks, cloth, stents and dental compositions.

Iodine is currently the leading contrast-giving atom for x-ray imaging techniques. The art discloses various iodine-containing materials for use as x-ray contrast agents, including materials provided in the form of nanopraticles.

EP 300828 by Jo. Klaveness and U.S. Pat. No. 4,826,689 by Violante et al. disclose methods for preparing x-ray contrast agent nanoparticles starting from water insoluble iodo-organic compounds, e.g. iodo esters, using precipitation procedures from organic solvents.

U.S. Pat. No. 5,451,393 by Liversidge et al. discloses the preparation of x-ray contrast agent colloidal particles starting from water insoluble iodo-organic compounds, e.g. iodinated aromatic compound, using a wet grinding method. According to this patent, grinding a contrast agent in a liquid medium in the presence of an appropriate surface modifier results in the formation of x-ray contrast agent colloidal particles of sizes less than 400 nm.

U.S. Pat. No. 5,019,370 by M. Jay et al. broadly describes biodegradable polymeric spheres of estimated average molecular weight about $10^5$ to $10^7$ Daltons and average diameter about 10-1000 nanometers carrying radiographic contrasting amount of a radiographically opaque element. According to the preparative procedure described in the patent, a polyester of tetraiodophenolphthalein (TIP) was prepared by reacting a solution of sodium TIP in 0.1 M borate buffer containing various quantities of dextran with succinyl chloride dissolved in dichloroethane. The polyester of TIP is about 58% iodine, by weight and precipitates as a monodisperse suspension with a mean particle diameter of 200 nm.

U.S. Pat. Nos. 5,565,215 and 5,160,725 describe radio opaque nanoparticles prepared by covalent binding of x-ray contrast agents to the surface of core nanoparticles containing surface functional groups. For example, U.S. Pat. No. 5,565,215 describes the possibility of binding radio opaque materials to hydroxyl groups belonging to the surface of nanoparticles.

Homo or co-polymerization of bulky iodine-containing vinylic monomers, using either melt polymerization or suspension polymerization procedures to form x-ray opaque microspheres of hundreds microns diameter for endovascular embolization or dentistry has also been proposed in the art [A. Jayakrishnan, B. Chithambara Thanoo, K. Rathinam and M. Mohanty. J. of Biomedical Materials Research 24, 993 (1990); M. Okamura, T. Yamanobe, T. Arai, H. Uehara, T. Komoto, S. Hosoi and T. Kumazaki. J. of Molecular Structure 602-603, 17 (2002)]. X-ray opaque microparticles of ca. 100 μm diameter were also prepared by a precipitation method, by dissolving a copolymer prepared from 2-methacryloyloxy-ethyl (2,3,5-triiodobenzoate) and methyl methacrylate in chloroform and converting the same into beads using a solvent evaporation technique [see K. Saralidze, Y. B. J. Aldenhoff, M. L. W. Knetsch and L. H. Koole, Biomacromolecules 4, 793 (2003)].

The term "nanoparticles", as used herein, broadly refers to particles having sizes ranging from approximately a few nanometers (5 nm) up to a few microns (5 μm). It has now been found that it is possible to polymerize vinyl monomers carrying iodine-substituted side groups to form polymeric nanoparticles having considerable iodine content, wherein said iodine-substituted groups are bonded to the polymer backbone via a cleavable bond. Accordingly, the iodine substituted groups may be detached from the polymeric chains without causing the fragmentation of the polymeric backbone.

Thus, in a first aspect, the present invention provides nanoparticles having average particle size of less than 2000 nm, and preferably in the range between 15 nm and 1000 nm, wherein said nanoparticles comprise a polymer having pendant cleavable iodine substituted groups. The term "pendant", as used herein, refers to the fact that the polymer contains iodine-substituted groups that are considered as side groups relative to the main backbone chain, such that their detachment from the polymer does not result in the fragmentation of the polymeric backbone chain. This structural property of the polymers according to the invention may be schematically illustrated for a hypothetical polymer whose repeat unit is A-G as follows:

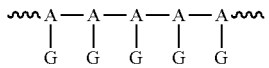

wherein G is the pendent iodine substituted group.

More preferably, the average particle size of the nanoparticles population provided by the invention is in the range between 15 nm and 500 nm, and even more preferably in the range between 15 nm and 100 nm, and most preferably in the range between 15 nm and 50 nm. The nanoparticles population provided by the present invention is characterized by a narrow particle size distribution, with a standard deviation which is not greater than 25%, and preferably not greater than 15%. The average particle size may be measured either by transmission electron microscopy (TEM) or by a coulter counter. TEM is used to determine the average particle size of a dry sample while coulter counter is used to measure the average particle size of wet samples.

The term "polymers", as used herein, includes homo-polymers and copolymers. In the case of a co-polymer, said co-polymer may be the polymerization product of two or more iodine substituted monomers, or alternatively, the polymerization product of at least one iodine substituted monomer with at least one bi-functional monomer that contains, in addition to its polymerizable functionality, a second reactive chemical group (e.g., glycidol methacrylate).

Preferably, the backbone chain of the polymer according to the present invention is selected from the group consisting of polyacrylate, polymethacrylate, polyacrylamide and polymethacrylamide backbone chains. A characteristic segment of polyacrylate and polymethacrylate backbone chains is illustrated by structure (A), wherein R is H or —$CH_3$, respectively, whereas a characteristic portion of polyacrylamide and polymethacrylamide backbone chains is represented by structure (B), wherein R is H or —$CH_3$, respectively:

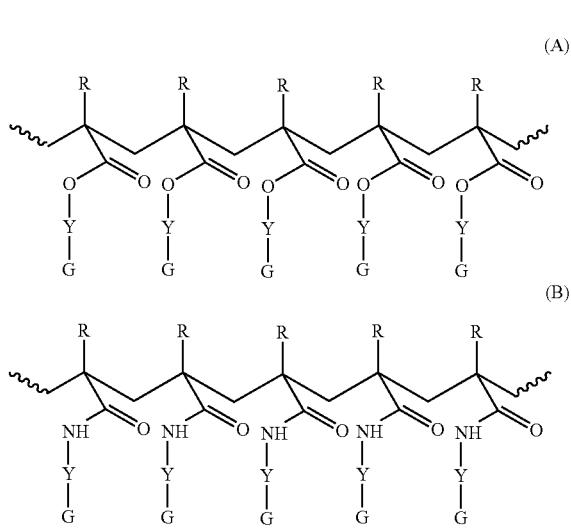

(A)

(B)

G is the pendant iodine substituted group, which is attached to the polymeric backbone chain through a linking moiety Y that contains a cleavable bond which is preferably an amide —NHC(O)— or an ester —C(O)O— bond, or, alternatively, Y may be null, in which case the iodine-substituted group G is linked to the polymeric backbone directly by the cleavable ester or amide functionality of the (meth)acrylate or (meth) acrylamide groups. The term "poly(meth)acrylate" and the like, when used herein, collectively refers to polyacrylate and polymethacrylate, whereas the term "poly(meth)acrylamide" and the like collectively refers to polyacrylamide and polymethacrylamide.

Particularly preferred nanoparticles provided by the present invention comprise a polymer that includes a repeat unit of the following structure:

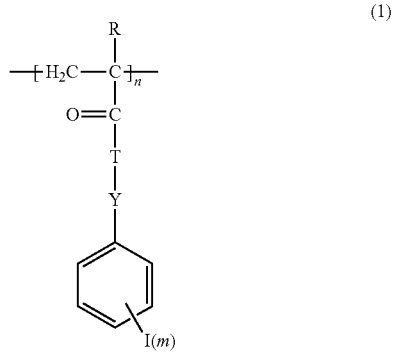

(1)

wherein R is H or methyl, n is the degree of polymerization, T is O or NH (for poly(meth)acrylate or poly(meth)acrylamide, respectively), m is an integer between 2 and 5 and Y is a linking moiety comprising a cleavable bond which is preferably an amide —NHC(O)— or an ester —C(O)O— bond, or, alternatively, Y may be null, in which case the iodine-substituted phenyl ring is directly linked to the polymeric backbone via the ester or amide functionality of the (meth) acrylate or (meth)acrylamide group, respectively. When m equals 2, 3 or 4, then the phenyl group may be further substituted by additional groups other than iodine. Preferred substituents include functional chemical groups, for example, —COOH, or the covalently coupled form of said functional groups with bio-reactive agent (e.g., proteins).

In the case of a copolymer, then the polymer chain includes, in addition to the repeat unit of formula (1), also a second repeat unit, and especially the following preferred repeat unit:

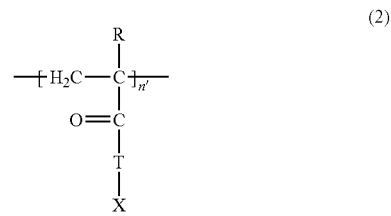

(2)

wherein R and T are as defined with respect to the structure formula (1), n' is the degree of polymerization, and X is a chemical moiety comprising a reactive functionality which is most preferably an oxirane group, or the coupled form of said functionality with a bioreactive agent, e.g., a protein. Preferably, n' is considerably smaller than n, such that the copolymer comprises not less than 70% by weight of the repeat unit of formula (1). Thus, in another embodiment, the present invention provides a random copolymer which is Poly(1-ran-2), wherein 1 and 2 represent the structures (1) and (2) above.

It should be noted that the nanoparticle of the present invention may be provided either in the form of a particle having a core which is made of the iodine-containing polymer described hereinabove (hereinafter sometimes abbreviated "core nanoparticle"), or in the form of a particle having a core made of a material which is different from said iodine-containing polymer, wherein said core material most preferably comprises silica or a magnetic substance such as iron oxide, wherein said core is coated with one or more layers of said iodine-containing polymer (herein sometimes abbreviated "core-shell nanoparticle").

The iodine content of the core nanoparticle is preferably not less than 50% (w/w), and more preferably not less than 60%. The iodine content of the core-shell nanoparticle is preferably not less than 5% (w/w), and more preferably not less than 20%.

The polymeric nanoparticles provided by the present invention are the free-radical chain polymerization product of at least one vinyl monomer, which is preferably a (meth) acrylate or a (meth)acrylamide monomer, having at least one iodine-substituted side group, wherein said side group is bonded to the polymerizable functionality of the monomer through a cleavable bond, which is preferably an amide or an ester bond. Thus, preferred (meth)acrylate and (meth)acrylamide monomers that may be suitably used for the free-radical chain polymerization according to the present invention may be represented by the structure of formula (3):

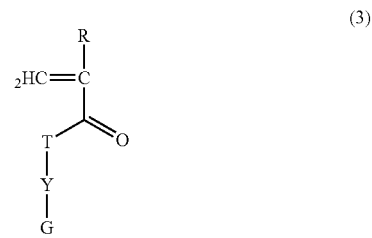

(3)

wherein R is H or methyl, T is O or NH, Y is a linking moiety comprising a cleavable bond which is preferably an amide —NHC(O)— or an ester —C(O)O— bond, or, alternatively, Y may be null, in which case the iodine-substituted group G is directly linked to the ester or amide functionality of the (meth)acrylate or (meth)acrylamide groups. The iodine-substituted group G is preferably a $C_3$-$C_8$ carbocyclic radical or aryl radical substituted by 2 to 5 iodine atoms. As used herein, the term "aryl" refers to substituted or unsubstituted carbocyclic aromatic systems containing one or more fused or non-fused phenyl rings. Accordingly, the nanoparticles of the present invention most preferably comprise a polymer having poly(meth)acrylate or poly(meth)acrylamide backbone chain, with pendant, iodine substituted aryl groups, which are linked to said backbone chain by means of amide or ester bonds.

It should be noted that when the number of iodine atoms attached to the aforementioned $C_3$-$C_8$ carbocyclic radical or aryl radical is less than 5, then said iodine-substituted group G may be optionally substituted with one or more substituents other than iodine. For example, the iodine-substituted group G may carry a reactive chemical group (e.g., —COOH), which is capable of covalently linking a bio-reactive agent (e.g. a protein).

Vinyl monomers having iodine substituted cleavable side groups, as represented by the structure of formula (3) above, which may be suitably used as starting materials according to the present invention, are readily prepared by methods known in the art [K. W. M. Davy, M. R. Anseau and C. Berry. J. of Dentistry 25 (6), 499 (1997); M. Okamura, T. Yamanobe, T. Arai, H. Uehara, T. Komoto, S. Hosoi and T. Kumazaki. J. of Molecular Structure 602-603, 17 (2002); K. W. M. Davy and M. R. Anseau. Polymer International 43, 143 (1997); A. Benzina, Marc-Anton B. Kruft, H. Van Der Veen, H. M. W. Bar, R. Blezer, T. Lindhout and L. H. Koole, J. of Biomedical Materials Research 32, 459 (1996); D. Horak, M. Metalova and F. Rypacek, J. of Biomedical Materials Research 34, 183 (1997)]. Briefly, these procedures are based on covalently binding iodine substituted compounds, and more specifically, iodine substituted carbocyclic aromatic compounds having suitable functionalities such as hydroxyl, carboxylate or amine groups, to vinylic monomers such as hydroxyethyl methacrylate (HEMA), acryloyl chloride, methacryloyl chloride and glycidyl methacrylate. The resulting monomers are (meth)acrylic and meth(acrylamide) monomers which carry cleavable iodine substituted side groups, and are therefore suitable for use in the preparation of the polymeric nanoparticles of the present invention.

A preferred class of iodine substituted (meth)acrylate and meth(acrylamido) monomers that may be used in a free-radical chain polymerization process to give the polymeric nanoparticles of the present invention are represented by the following structure of formula (4):

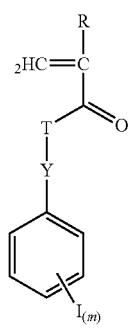

(4)

wherein R is H or methyl; T is O or NH; Y is a linking moiety comprising a cleavable bond which is preferably an amide —NHC(O)— or an ester —C(O)O— bond, or, alternatively, Y may be null, in which case the iodine-substituted phenyl group is directly linked to the ester or amide functionality of the (meth)acrylate or (meth)acrylamide groups; m is an integer in the range between of 2 and 5, and wherein when m equals 2 or 3, then the phenyl ring in the structure of formula (4) is optionally substituted by one or two substituents other than iodine. For example, the phenyl ring may be substituted by carboxylic acid (—COOH) group.

The synthesis of especially preferred monomers of the formula (4) above are illustrated in the following reaction schemes.

The monomer MAAATIB [3-(methacryloylamido)-2,4,6-triiodobenzoic acid] was synthesized according to D. Horak, M. Metalova and F. Rypacek, J. of Biomedical Materials Res. 34, 183-188 (1997), through the following scheme:

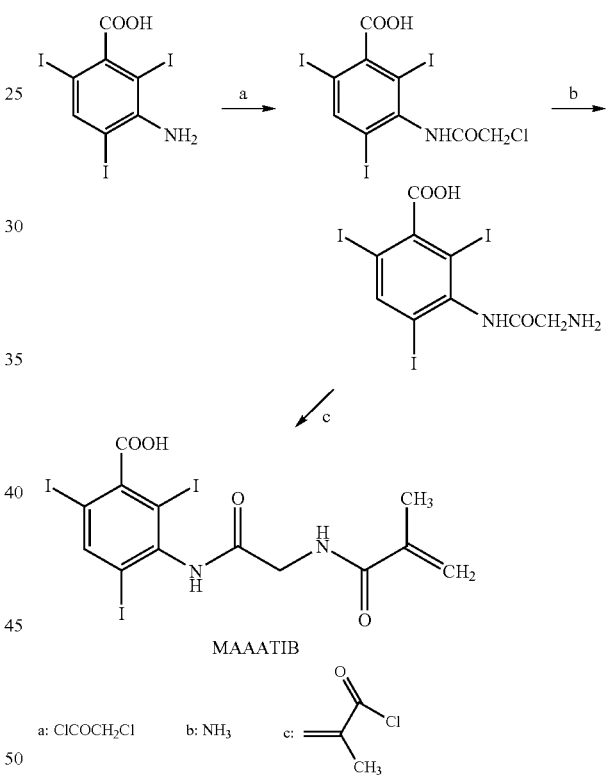

The monomer MAOETIB [2-methacryloyloxyethyl (2,3,5-triiodobenzoate)] was synthesized according to K. W. M. Davy, M. R. Anseau and C. Berry, J. of Dentistry 25 (6), 449-505 (1997), through the following scheme (RT means room temperature, HEMA means hydroxyethyl methacrylate:

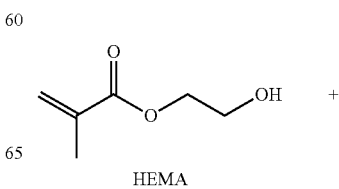

-continued

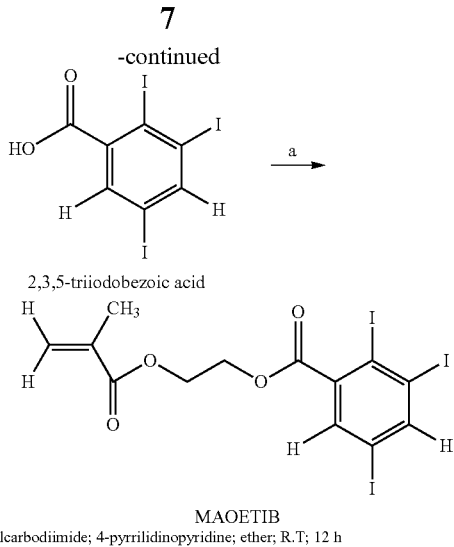

2,3,5-triiodobezoic acid

MAOETIB a: 1,3-dicyclohexylcarbodiimide; 4-pyrrilidinopyridine; ether; R.T; 12 h The monomers TIPMA (2,4,6-triiodophenyl-methacrylate) and TIPA (the corresponding acrylate) were synthesized according to M. Okamura et al. [J. of Molecular Structure 602-603, 17 (2002)], by the following scheme:

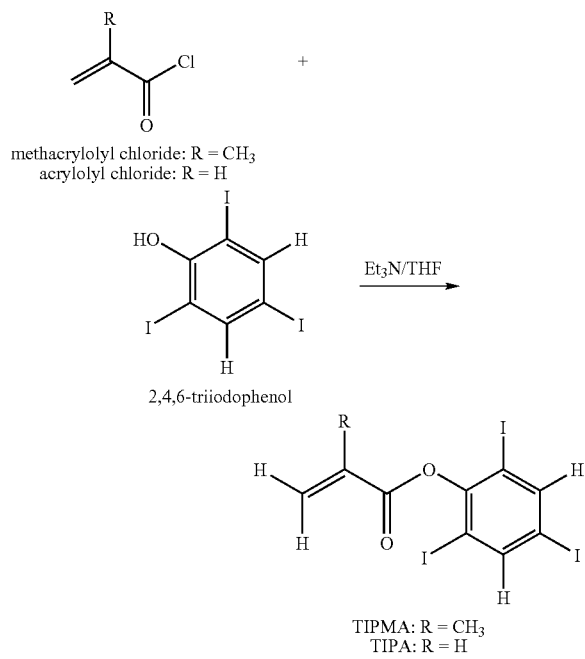

methacrylolyl chloride: R = CH$_3$
acrylolyl chloride: R = H 2,4,6-triiodophenol

TIPMA: R = CH$_3$
TIPA: R = H

In another aspect, the present invention provides a process, which comprises providing a vinyl monomer having at least one iodine-substituted side group, wherein said side group is bonded to the polymerizable functionality of said monomer through a cleavable bond (as represented, for example, by structures (3) and (4) above), and polymerizing said monomer in the presence of a free radical initiator, to form nanoparticles having an average size of less than 2000 nm.

When core-shall nanoparticles are intended, the starting core particles (e.g., silica or iron oxide nanoparticles) are introduced into the reaction vessel to allow the polymerization product to coat the same. Optionally, a second monomer is present in the reaction mixture, to allow the formation of a copolymer, wherein said second monomer is preferably a bi-functional monomer that contains, in addition to its polymerizable functionality, a second reactive chemical group. Especially preferred second monomer is glycidol methacrylate.

The free-radical polymerization is most preferably accomplished using either emulsion or dispersion polymerization procedures. The specific class of monomers of formula (4) may be used for preparing the polymers of formula (1) above. Emulsion polymerization processes in general are based on polymerization of water insoluble monomer/s, in the absence or presence of an organic phase, in an aqueous continuous phase containing water soluble initiator and a surfactant; dispersion polymerizations in general are based on homogeneous polymerization system wherein the monomer/s, the initiator and the stabilizer used for preventing agglomeration are all soluble in the organic continuous phase. The growing oligoradicals at some size, due to their low solubility in the continuous phase, precipitate as new nuclei which then grow to their final size.

Suitable initiators that may be used according to the free-radical polymerization process provided by the present invention are well known in the art and include potassium persulfate, sodium persulfate, hydrogen peroxide, redox initiators such as sodium hydrosulfite and potassium persulfate for emulsion polymerization and benzoyl peroxide and azobisisobutyronitrile for dispersion polymerization.

The emulsion polymerization is carried out by dissolving in an aqueous medium the initiator and the surfactant, followed by the addition of the monomer or an organic solution thereof to the aqueous phase. To this end, solid monomers may be suitably pre-dissolved in a water-immiscible organic solvent, for example, an aromatic hydrocarbon such as toluene and chlorobenzene, or an halogenated alkane such as methylene chloride, following which the resulting organic solution is added into the reaction vessel containing the aqueous phase. The concentration of the monomer is preferably in the range of 1 to 15% (weight percent relative to the solvent). The concentration of the initiator is typically in the range of 0.25 to 15% relative to the weight of the monomer. The concentration of the surfactant is preferably in the range of 0.1 to 15% of the weight of the solvent. A suitable surfactant is, for example, sodium dodecylsulfate. The reaction may be carried out at room temperature and more preferably under heating.

The dispersion polymerization is carried out by mixing the monomer, the initiator and the stabilizer in an organic solvent, preferably under heating, for a sufficient period which may last several hours. A suitable organic solvent may be selected from the classes of nitrites, ketones and amides; specifically, acetonitrile, methyl ethyl ketone, N,N-dimethylforamide as well as toluene and 2-methoxyethanol may be mentioned. The concentration of the monomer is preferably in the range of 1 to 15% (weight percent relative to the solvent). The concentration of the initiator, which is most preferably benzoyl peroxide, is typically in the range of 0.25 to 15% relative to the weight of the monomer. The concentration of the stabilizer is preferably in the range of 0.1 to 15% of the weight of the solvent. As a stabilizer, polyvinyl pyrrolidone or commercially available copolymers of ethylene oxide and propylene oxide (Pluronic®) can be used.

Having completed the polymerization reaction, the resulting nanoparticles are washed by methods such as centrifugation, dialysis or by columns containing an appropriate packing materials such as sepharose 4B.

The nanoparticles of the present invention are most preferably preserved in the form of a suspension, using either an aqueous or organic medium as the liquid vehicle, optionally in the presence of a stabilizer (which is generally a surfactant) to prevent the agglomeration of said nanoparticles. The exact identity of the liquid medium is determined according to the intended use of the nanoparticles, as will be discussed in more detail below. However, if desired, the nanoparticles may be also provided in the form of a dry powder, optionally in the presence of a dispersant, which powder may be obtained by known lyophilization procedures.

If desired, the surface of the nanoparticle provided by the present invention may be subjected to functionalization for improving the biocompatibility thereof, and for allowing the binding of an homing agent thereto. The functionalization may be accomplished in any of the following ways: (1) Homopolymerization of acrylate monomer containing in addition to the iodine atoms functional groups such as carboxylates; (2) Coating of the x-ray contrast agent particles with functional surfactants or polymers such as proteins or polycarbohydrates; (3) Covalent binding of bi-functional polymers to functional x-ray contrast agent particles, e.g. binding $\alpha$-amino, $\omega$-carboxylate polyethylene glycol to particles containing carboxylate groups. Tissue-specific x-ray contrast agent nanoparticles are formed by binding to the surface of the particles, via the functional group, an appropriate homing agent such as drugs, proteins, antigens and antibodies. Drugs (e.g. aspirin) for controlled release purposes could also be encapsulated or bonded to the nanoparticles. Accordingly, the process for preparing the nanoparticles of the invention may further comprise the modification of the surface of the said nanoparticles by coating the same with an agent selected from the group consisting of surfactants, proteins and polysaccharides, to form surface-coated nanoparticles. The process provided by the present invention may also include covalently binding to the surface of the nanoparticles or the coated nanoparticles a bi-functional polymer through the first functional group of said bi-functional polymer, and subsequently optionally reacting the second functional group of said bi-functional polymer with an homing agent selected from the group consisting of drugs, proteins, antigens and antibodies.

The nanoparticles provided by the present invention may be used as x-ray contrast agent in various radiographic applications, e.g. medical imaging and diagnostic radiology, dental compositions and the x-ray detection of plastics, inks, and stents, etc. As indicated above, the nanoparticles comprise a polymer having pendant iodine substituted groups that are linked to the backbone of the polymeric chain through a cleavable (e.g., hydrolysable) bond. Under appropriate conditions, e.g. in the presence of basic conditions, or enzymes such as esterases, the pendant iodine containing groups are released from the backbone of the polymeric chains. The released iodine containing ligand, after hydrolysis of the cleavable bonds, is an organo-iodine x-ray contrast agent, which is most preferably selected from the group consisting of 2,4,6-triiodobenzoic acid, 3-amino-2,4,6-triiodobenzoic acid, 3-acetamide-2,4,6-triiodobenzoic acid, and 3-(methacryloylamido)-2,4,6-triiodobenzoic acid.

When intended for medical imaging and diagnostic radiology, the x-ray contrast agent nanoparticles of the invention may be introduced into the subject by any convenient and efficient means. Suitable compositions comprising said nanoparticles may be especially formulated for local administration or for oral administration. Thus, in another aspect, the present invention provides a radiographic composition comprising a radiographically effective amount of the nanoparticles of the present invention as X-ray contrast agent and a physiologically acceptable liquid carrier.

The term "local administration" includes all possible means for administering the x-ray contrast agent nanoparticles of the invention at, or close to, the targeted area. This term is not limited to syringe injection alone, but also encompasses the use of all commonly used mechanical and electromechanical pumping devices, controlled-release devices, infusion systems, and other related mechanisms for local delivery of therapeutic agents.

Preferably, the X-ray contrast composition of the invention is an injectable formulation, wherein the nanoparticles are suspended in a saline (sodium chloride/water) solution that may optionally contain a physiologically acceptable stabilizer, for example, polyvinylpyrrolidone. Another suitable liquid carrier is a phosphate buffer at physiological pH. The injectable formulations can be sterilized, for example, by filtration through a bacterial-retaining filter, or by incorporating sterilizing agents therein. These formulations may also contain preservatives, wetting agents, emulsifying agents, dispersing agents and surfactants.

Liquid dosage forms for oral administration include suspensions comprising the x-ray contrast agent nanoparticles. In addition to the x-ray contrast agent nanoparticles, the liquid dosage form may contain inert diluents commonly used in the art. Besides inert diluents, the oral compositions may also include adjuvants such as wetting agents, emulsifying and suspending agents, buffering agents, sweetening, flavoring and perfuming agents.

Typically, the nanoparticles contrast agents of the invention are administered in an amount of about 0.5 to 1500 milligrams/kg of body weight. The selected dosage regime will depend on the identity of the particular nanoparticle, the route of administration and other factors associated with the patient being treated.

The administration of the nanoparticles contrast agents of the invention to the patient is followed by a suitable waiting period, allowing the contrast agent to reach the targeted body organ. The X-ray imaging may then be performed using techniques well known in the art of radiology, such as X-ray imaging and computerized tomography (CT).

In the drawings:

FIG. 1 is an histogram demonstrating the size and size distribution of the nanoparticles according to the invention.

Figure 2A:
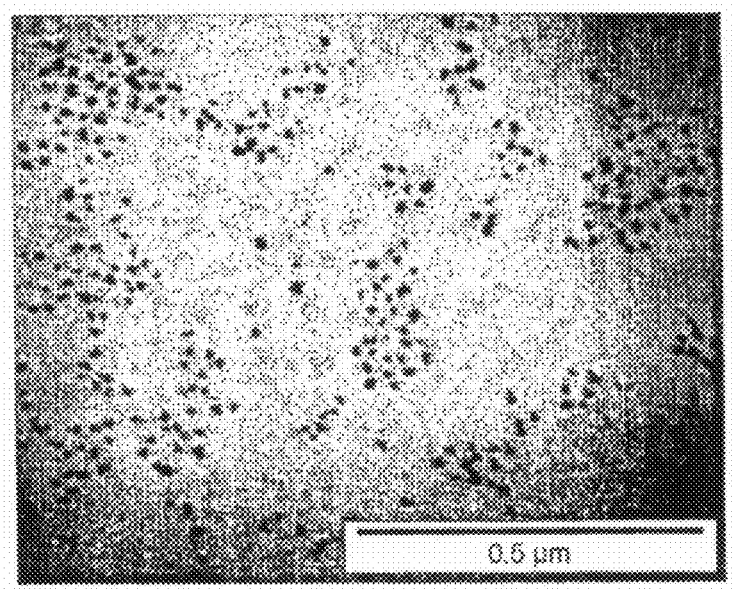
Figure 2B:
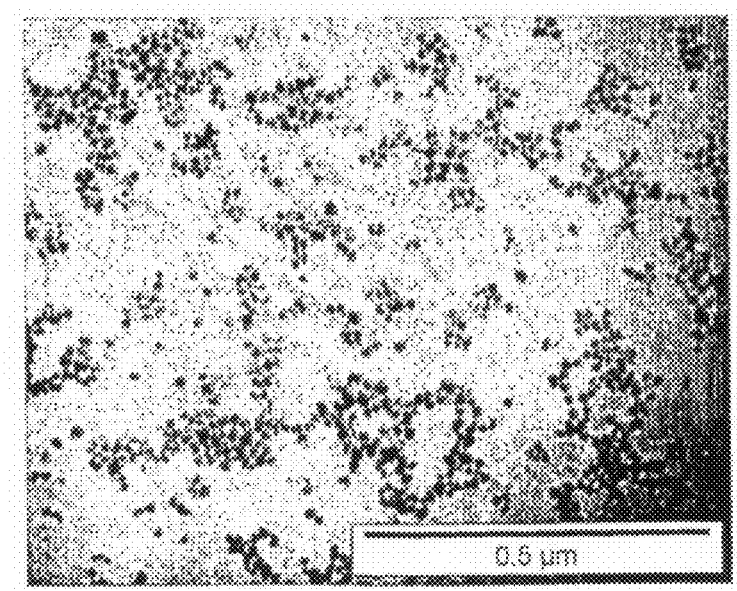

FIGS. 2A and 2B demonstrate TEM pictures of magnetic nanoparticles and the coated core-shell iron oxide nanoparticles, respectively.

EXAMPLES

Example 1

Emulsion Polymerization of MAOETIB

Into a vial containing 20 ml 1% (w/v) sodium dodecylsulfate (SDS) aqueous solution and 8 mg of potassium persulfate, 3 ml toluene solution containing 400 mg MAOETIB were introduced. The mixture was then shaken at 73° C. for 12 h. The organic phase containing toluene and excess monomer was then extracted from the aqueous phase. The average size and size distribution of the polyMAOETIB nanoparticles dispersed in the aqueous phase, as measured by sub-micron particle analyzer (Coulter N4, Coulter, England), was 30±3 nm, as shown in FIG. 1. FIG. 1 is an histogram demonstrating the size and size distribution of the poly MAOETIB nanoparticles formed according to example 1.

The iodine percent of the water washed, dried polyMAOETIB nanoparticles formed according to example 1 was ca. 61%.

The x-ray imaging absorption ability of various concentrations of these nanoparticles dispersed in water as measured with CT (MARCONI, HeliCAT II) in Hounsfield Units (HU) are shown in Table 1.

TABLE 1 x-ray imaging absorption of various concentrations of the polyMAOETIB nanoparticles dispersed in water.

| [PolyMAOETIB nanoparticles] (mg/ml) | HU |
|---|---|
| 0 (only water) | 0 |
| 0.5 | 6 ± 3 |
| 1 | 16 ± 3 |
| 2 | 42 ± 4 |
| 4 | 115 ± 3 |
| 8 | 185 ± 5 |
| 16 | 362 ± 2 |

Example 2

For long storing, or for medical uses (wherein excess SDS has to be removed) an appropriate stabilizer or surfactant, e.g. 0.5% polyvinylpyrrolidone (average m.w. 40,000) was added to the PolyMAOETIB nanoparticles dispersion in the aqueous phase. Free SDS was then removed from the aqueous dispersion by dialysis. The average diameter, size distribution and the x-ray imaging absorption ability of the nanoparticles did not change due to this operation.

Example 3

Example 1 was repeated by varying the concentration of the monomer (the monomer's quantity introduced into the vessel was in the range between 25 mg and 1 g), to obtain particles of average sizes between ca. 15 nm up to ca. 400 nm.

Example 4

Emulsion Polymerization in the Melt State of MAOETIB

A vial containing 20 ml 1% (w/v) sodium dodecylsulfate (SDS) aqueous solution, 8 mg potassium persulfate and 400 mg MAOETIB was shaken at 100° C. for 12 h. Particles of broad size distribution, between ca. 20 nm to ca. 1000 nm were formed. For long storing of the PolyMAOETIB nanoparticles dispersion in the aqueous phase an appropriate stabilizer or surfactant, e.g. polyvinylpyrrolidone (final concentration 0.5%) was added, and the free SDS was then removed from the aqueous dispersion by dialysis.

Example 5

Dispersion Polymerization of MAOETIB

A vial containing 0.1 g polyvinyl pyrrolidone (m.w. 360,000), 0.5 g MAOETIB and 0.01 g benzoyl peroxide dissolved in 10 ml 2-methoxyethanol was shaken at 73° C. for approximately 12 h. The formed polyMAOETIB particles were then extensively washed by centrifugation cycles with 2-methoxyethanol and then water, or by extensive dialysis against water. The average size and size distribution of the polyMAOETIB particles dispersed in the continuous phase was 400 (±10%) nm.

Example 6

Example 5 was repeated by varying the weight of the monomer (in the range between 0.1 and 1 g) and the molecular weight of the PVP surfactant, to obtain particles of average sizes between ca. 400 nm up to ca. 1400 nm.

Example 7

Coating of Nanoparticles (Magnetic Iron Oxide and Silica) with PolyMAOETIB

Example 7-A

Coating of Magnetic Iron Oxide Nanoparticles with PolyMAOETIB

Example 1 was repeated substituting the water with magnetic iron oxide nanoparticles (ca. 15 nm diameter) dispersed in the water (2.5 mg/ml). The formed polyMAOETIB coated core-shell magnetic nanoparticles were washed by high gradient magnetic field (HGMF). The % I of the polyMAOETIB coating of the core-shell nanoparticles was 24%. For long storing, or for medical uses (wherein excess SDS has to be removed) an appropriate stabilizer or surfactant, e.g. 0.5% polyvinylpyrrolidone (average m.w. 40,0000) was added to the PolyMAOETIB magnetic core-shell nanoparticles dispersion in the aqueous phase. Free SDS was then removed from the aqueous dispersion by HGMF.

FIG. 2 demonstrates TEM pictures of the iron oxide magnetic nanoparticles (A) and the polyMAOETIB coated core-shell iron oxide nanoparticles (B).

The x-ray imaging absorption ability of various concentrations of these core-shell magnetic nanoparticles dispersed in water as measured with CT (MARCONI, HeliCAT II) in Hounsfield Units (HU) are shown in Table 2.

TABLE 2 x-ray imaging absorption of various concentrations of the iron oxide magnetic nanoparticles and the polyMAOETIB coated core-shell iron oxide nanoparticles dispersed in water.

| Nanoparticles Concentration (mg/ml) | HU Iron oxide magnetic nanoparticles | HU PolyMAOETIB coated core-shell iron oxide magnetic nanoparticles containing 24% I |
|---|---|---|
| 0.5 | 4 ± 2 | 9.5 ± 0.7 |
| 1 | 4 ± 2.1 | 13 ± 1.2 |
| 2 | 4.5 ± 0.8 | 18 ± 1.5 |
| 4 | 6.4 ± 0.8 | 34.9 ± 1.1 |
| 8 | 13.5 ± 2.4 | 80 ± 2 |
| 16 | 16 ± 1.5 | 145 ± 0.8 |

Similar polyMAOETIB coatings onto iron oxide particles of various sizes, from ca. 15 nm up to ca. 500 nm, were also performed.

Example 7-B

Coating of Silica Nanoparticles with PolyMAOETIB

Example 7-A was repeated substituting the iron oxide nanoparticles for silica nanoparticles of ca. 200 nm diameter (formed by a process similar to the Stober method, see W. Stober, A. Fink and E. J. Bohn, J. Colloid Interface Science 26, 62 (1968). The coated silica particles were washed by several centrifugation cycles with water. Similar x-ray imaging absorption abilities of these polyMAOETIB silica coated nanoparticles were measured.

Example 8

Example 7 was repeated in the presence of various concentrations of the monomer MAOETIB, thereby, PolyMAOETIB coated core-shell iron oxide magnetic nanoparticles containing different iodine concentrations were produced, as shown in Table 3.

TABLE 3

% I of PolyMAOTIB coated core-shell iron oxide nanoparticles prepared in the presence of various concentrations of MAOETIB.

| [MAOETIB] (mg) | % [I] |
|---|---|
| 200 | 5.0 |
| 400 | 24 |
| 600 | 43 |
| 800 | 45 |

Example 9

Emulsion Polymerization in the Melt State of MAAATIB
[3-(methacryloylamido)-2,4,6-triiodobenzoic acid]

A vial containing 8 mg potassium persulfate and 400 mg MAAATIB dissolved in 20 ml 1% (w/v) sodium dodecylsulfate (SDS) deairated aqueous solution was shaken at 100° C. for 12 h. Particles in sizes ranging between ca. 15 nm to ca. 2000 nm were formed. For long storing of the Poly MAAATIB nanoparticles dispersion in the aqueous phase polyvinylpyrrolidone (final concentration 0.5%) was added, and the SDS was then removed from the aqueous dispersion by dialysis.

Example 10

Dispersion Polymerization of TIPMA (2,4,6-triiodophenyl-methacrylate) and TIPA (2,4,6-triiodophenyl-acrylate)

A vial containing 0.1 g polyvinylpyrrolidone (m.w. 360,000), 0.4 g TIPMA (or TIPA) and 10 mg benzoyl peroxide dissolved in 10 ml of deairated acetonitrile was shaken at 73° C. for 12 h. PolyTIPMA (or polyTIPA) particles containing ca. 70-72% I in sizes ranging between ca. 15 nm to ca. 2000 nm were formed. The acetonitrile was then replaced with water containing 0.5% polyvinylpyrrollidone by dialysis.

Example 11

Encapsulation of Drugs

Examples 1 and 5 were repeated in presence of 40 mg adriamycin. Similar nanoparticles containing adriamycin were produced.

Example 12

Functionalization of the X-Ray Imaging Nanoparticles

Derivatization of the organic iodine nanoparticles was performed with reagents such as proteins, polysaccharides and functional polymers.

For example, the following typical surface modification procedures are hereby described:

12-A. Derivatization of the x-ray opaque nanoparticles with proteins, i.e. Human Serum Albumin (HSA) and Gelatin 12-A-I. In a typical experiment, HSA conjugated polyMAOETIB nanoparticles were formed by adding 75 mg Human Serum Albumin (HSA) into 30 ml aqueous dispersion of the polyMAOETIB nanoparticles (2.5 mg/ml) prepared according to example 1 & 2. The mixture was then shaken at 60° C. for ca. 4 h. Then, the mixture was cooled to room temperature. The HSA coated particles were then washed extensively by dialysis. The washed coated nanoparticles aqueous dispersion was then stored at 4° C.

12-A-II. In a typical experiment, Gelatin conjugated polyMAOETIB nanoparticles were prepared according to the description in experiment 12-A-I substituting HSA for gelatin.

12-A-III. Aldehyde derivatized polyMAOETIB nanoparticles were prepared by adding to the protein conjugated polyMAOETIB nanoparticles prepared according to 12-A-I and 12-A-II, before drying, glutaraldehyde (final concentration 0.5%). Then, the mixture was shaken at room temperature for 4 h. Unreacted glutaraldehyde was then removed from the aldehyde conjugated protein polyMAOETIB nanoparticles by extensive dialysis against water. The washed nanoparticles was then stored at 4° C.

12-A-IV. Protein and aldehyde protein coated magnetic core-shell iron oxide/polyMAOETIB nanoparticles were prepared by repeating experiments 12-A-I to 12-A-III substituting the polyMAOETIB nanoparticles with the magnetic core-shell iron oxide/polyMAOETIB nanoparticles prepared according to example 7-A.

12-A-V. Protein coated polyMAAATIB nanoparticles, polyTIPMA nanoparticles and polyTIPA nanoparticles were prepared by repeating experiments 12-A-I and 12-A-II substituting the polyMAOETIB nanoparticles with polyMAAATIB nanoparticles, polyTIPMA nanoparticles and polyTIPA nanoparticles prepared according to examples 9 and 10, respectively.

12-B. Derivatization of the x-ray opaque nanoparticles with polysaccharides, i.e. chitosan and cellulose 12-B-I. Derivatization of the x-ray opaque nanoparticles with chitosan.

In a typical experiment, 1 ml of 0.5% (w/v) chitosan (primary amino polysaccharide) aqueous solution at pH3.0 was introduced into 5 ml of the x-ray opaque nanoparticles prepared according to example 7-A at pH 3.0. The pH of the suspension was then gradually raised to ca. pH 7, in order to precipitate the chitosan onto the ferrite particles. The chitosan coated particles were then extensively washed with HGMF with water and the washed coated magnetic nanoparticles were then stored at 4° C.

12-B-II. Derivatization of the x-ray opaque nanoparticles with cellulose

In a typical experiment, 1 ml of 0.5% (w/v) cellulose xanthate aqueous solution was introduced into 5 ml of the x-ray opaque nanoparticles prepared according to example 7-A. The suspension was then heated to ca. 80° C. and shaken then for another 4 h in order to hydrolyzed the cellulose xanthate. The cellulose coated particles were then extensively washed from free cellulose with water with HGMF. The washed coated magnetic nanoparticles were then stored at 4° C.

12-C. Derivatization of the x-ray opaque nanoparticles with functional polyethylene glycols ∝-Amino, ω-carboxylate polyethylene glycol (m.w. 5,000) was bonded via its primary amine group to polyMAAATIB through the carbodiimide activation method, according procedures known in the literature [O. Melamed and S. Margel, J. of Colloid and Interface Science 241, 357 (2001)]. In a typical experiment, 60 mg NHS (acetic acid N-hydroxysuccinimide ester) and 40 mg CDC (carbodiimide metho-p-toluenesulfonate) were added into 15 ml aqueous buffer solution at pH 5.0 containing polyMAAATIB nanoparticles (50 mg) prepared according to example 9. The nanoparticles suspension was then shaken at room temperature for 3 h. 5 mg of the ∝-amino, ω-carboxylate polyethylene glycol dissolved in 2 ml phosphate buffer (0.1M at pH7.5) were then added to the activated nanoparticles. The suspension was then shaken for another 12 h. The ω-carboxylate polyethylene glycol coated particles were then extensively washed by dialysis, and then stored at 4° C.

Example 13

Coupling of Amino Ligands (i.e. Proteins or Drugs) to the Functional Derivative X-Ray Imaging Particles 13-A. Coupling of amino ligands (i.e. proteins or drugs) to the amine derivative x-ray imaging particles In general, the amine derivatized x-ray imaging particles were shaken at room temperature (or other desired temperature) for a few hours with an appropriate activating reagent (i.e. bis[sulfosuccinimidyl]suberate) in phosphate buffer saline (PBS pH7.4). Unbound activating reagent was then removed by HGMF or dialysis against PBS. The activated particles were then bonded with amino ligands (i.e. proteins or drugs) by shaking them at room temperature (or other desired temperature) for a few hours with a desired protein (or drugs) and then for another few hours with a blocking reagent (e.g. glycine, ethanol amine at pH7, etc.) in PBS (or other physiological solution). Unbound protein (or drug) was then removed by HGMF or dialysis against PBS (or other physiological solution). The conjugated particles were then kept in PBS (or water, or other physiological solution) at 4° C.

In a typical experiment, 1 mg of the amine-derivatized x-ray imaging particles prepared according to examples 1, 2 and 7 were shaken at room temperature for 4 h with 0.05 mg of the activating reagent bis[sulfosuccinimidyl]suberate. Unbound activating reagent was then removed by HGMF or dialysis against PBS. The activated derivatized particles were then shaken at room temperature for 4 h with 0.05 mg trypsin in 5 ml PBS. Residual activating groups on the particles were then blocked by adding to the shaken conjugated nanoparticles 20 mg glycine. After another 2 h, unbound trypsin and glycine were then removed by HGMF or dialysis against PBS. The trypsin conjugated particles were then kept in PBS (or water, or other physiological solution) at 4° C.

Protein A and adriamycin were also conjugated to the x-ray contrast agent particles by using a similar procedure.

13-B. Coupling of amino ligands (i.e. proteins and drugs) to the aldehyde-derivatized x-ray imaging nanoparticles In general, the aldehyde derivatized x-ray imaging particles were shaken at room temperature (or other desired temperature) for few hours with the desired protein in PBS (or other physiological solution). Unbound protein was then removed by HGMF or dialysis against PBS. Residual aldehyde groups were then blocked with amino ligands, such as BSA, hydroxylamine or ethanol amine in physiological pH. The protein conjugated particles were then kept in PBS (or water, or other physiological solution) at 4° C.

In a typical experiment, 1 mg of the aldehyde-derivatized x-ray contrast agent particles prepared according to examples 1, 2 and 7 were shaken at room temperature for 4 h with 0.5 mg trypsin in 5 ml PBS. Unbound trypsin was then separated by HGMF or dialysis against PBS. Residual aldehyde groups on the particles were then blocked by shaking the conjugated particles at room temperature for 4 h with. BSA (1%) in PBS. Unbound BSA was then removed by HGMF or dialysis against PBS. The trypsin conjugated particles were then kept in PBS (or water, or other physiological solution) at 4° C.

Protein A and adriamycin were also conjugated to the x-ray contrast agent particles by using a similar procedure.

13-C. Coupling of amino ligands (i.e. proteins or drugs) to the carboxylate derivatized x-ray imaging particles In general, the carboxylate derivatized x-ray imaging particles were shaken at room temperature (or other desired temperature) for a few hours with NHS and CDC aqueous buffer at pH5.0. Unbound activating reagent was then removed by HGMF or dialysis against PBS. The activated particles dispersed in PBS (or other physiological solution) were then bonded with amino ligands (i.e. proteins or drugs) by shaking them at room temperature (or other desired temperature) for a few hours with a desired protein (or drugs) and then for another few hours with a blocking reagent (e.g. glycine, ethanol amine at pH 7, etc.). Unbound protein (or drug) was then removed by HGMF or dialysis against PBS (or other physiological solution). The conjugated particles were then, kept in PBS (or water, or other physiological solution) at 4° C.

In a typical experiment, 20 mg NHS and 15 mg CDC were added into 15 ml aqueous buffer solution at pH 5.0 containing the nanoparticles (15 mg) prepared according to example 12-C. The nanoparticles suspension was then shaken at room temperature for 3 h. Unbound activating reagent was then removed by HGMF or dialysis against PBS. The activated derivatized particles were then shaken at room temperature for 4 h with 1 mg trypsin in 5 ml PBS. Residual activating groups on the particles were then blocked by adding to the shaken conjugated nanoparticles 10 mg glycine. After another 2 h, unbound trypsin and glycine were then removed by HGMF or dialysis against PBS. The trypsin conjugated particles were then kept in PBS (or water, or other physiological solution) at 4° C.

Protein A and adriamycin were also conjugated to the x-ray contrast agent particles by using a similar procedure.

Example 14

Example 1 was repeated, in the presence of 20 mg of glycidol methacrylate in the toluene solution, to form the corresponding copolymer.

Example 15

Injectable Formulation

PolyMAOETIB nanoparticles, prepared in accordance with Example 1, were dispersed in saline (water containing 0.85% NaCl) in the presence of polyvinylpyrrolidone (MW=55,000, at a concentration of 0.5%). The concentration of the nanoparticles was 3 mg/ml. The resulting dispersion was sterilized by passing the same through a filter paper containing holes of 0.2 microns. The filtered saline dispersion of the nanoparticles is ready for injection.

The invention claimed is:

1. Nanoparticles having an average particle size of less than 2000 nm, wherein said nanoparticles comprise a polymer having pendant cleavable iodine substituted groups.

2. Nanoparticles according to claim 1, wherein the polymer has a backbone chain selected from the group consisting of polyacrylate and polymethacrylate backbone chains, as represented by structure (A), and polyacrylamide and polymethacrylamide backbone chains, as represented by structure (B):

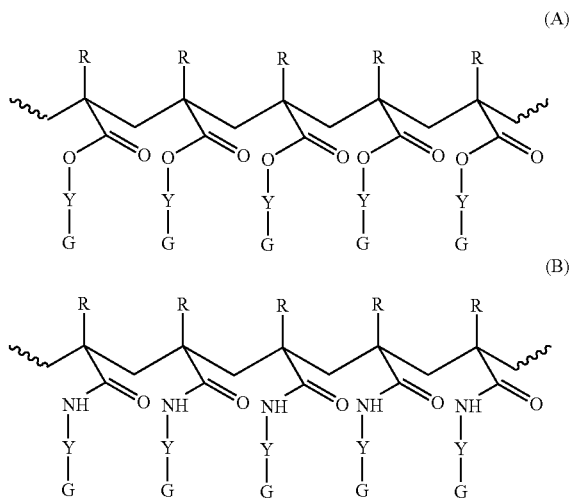

wherein R is H or —CH$_3$, G is the pendant iodine substituted group, which is attached to the polymeric backbone chain through a linking moiety Y that contains a cleavable bond, or, alternatively, Y may be null, in which case the iodine-substituted group G is linked to the polymeric backbone directly by the cleavable ester or amide functionality of the (meth)acrylate or (meth)acrylamide groups of structures A and B, respectively.

3. Nanoparticles according to claim 2, wherein the linking moiety Y comprises a cleavable bond which is an ester or an amide bond.

4. Nanoparticles according to claim 1, which comprise a polymer that includes the following repeat unit:

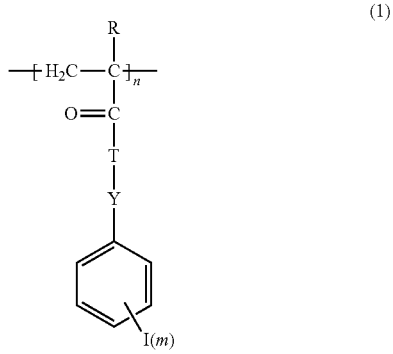

(1)

wherein R is H or methyl, n is the degree of polymerization, T is O or NH for poly(meth) acrylate or poly(meth)acrylamide, respectively, m is an integer between 2 to 5 and Y is a linking moiety comprising a cleavable bond which is an amide —NHC(O)— or an ester —C(O)O— bond, or, alternatively, Y may be null, in which case the iodine-substituted phenyl ring is directly linked to the polymeric backbone via the ester or amide functionality of the (meth)acrylate or (meth)acrylamide group, respectively, and wherein when m equals 2 or 3, then the phenyl group may be further substituted by additional groups other than iodine.

5. Nanoparticles according to claim 4, which comprise a polymer selected from the group consisting of poly[3-(methacryloylamido)-2,4,β-triiodobenzoic acid], poly[2-methacryloyloxyethyl (2,3,5-triiodobenzoate)], poly[2,4,6-triiodophenyl-methacrylate] and poly[2,4,6-triiodophenyl-acrylate].

6. Nanoparticles according to claim 1, wherein the polymer having pendant cleavable iodine substituted groups forms the core of said nanoparticles.

7. Nanoparticles according to claim 1, wherein the polymer having pendant cleavable iodine substituted groups is provided in the form of one or more layers coating the core of said nanoparticles.

8. Nanoparticles according to claim 7, wherein the core of said nanoparticles comprises silica or a magnetic substance.

9. Nanoparticles according to claim 1, wherein the particle average size of the nanoparticles population is in the range between 15 nm and 1000 nm.

10. Nanoparticles according to claim 9, wherein the average particle size of the nanoparticles population is in the range between 15 nm and 500 nm.

11. Nanoparticles according to claim 4, wherein the polymer is a copolymer which includes also the following repeat unit:

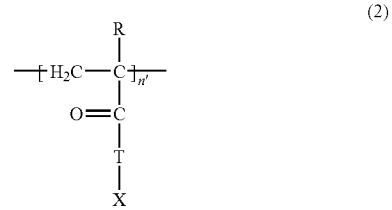

(2)

wherein R and T are as defined in claim 4 with respect to the structure formula (1), $n^1$ is the degree of polymerization, and X is a chemical moiety comprising a reactive functionality, or the coupled form of said functionality with a bioreactive agent.

12. Nanoparticles according to claim 11, wherein R is —CH$_3$, T is O and X comprises an oxirane group or its coupled form with a protein.

13. Nanoparticles according to claim 1, wherein the polymer is a free-radical chain polymerization product of one or more vinyl monomers.

14. Nanoparticles according to claim 13, wherein the vinyl monomer is selected from the group consisting of acrylate, methacrylate, acrylamide and methacrylamide monomers, wherein said monomer has at least one iodine-substituted side group, wherein said side group is bonded to the polymerizable functionality of said monomer by means of a cleavable bond.

15. Nanoparticles according to claim 13, wherein the monomer is represented by the following structure (3):

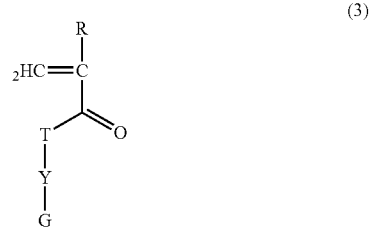

(3)

wherein R is H or methyl, T is O or NH, G is a iodine substituted group, Y is a linking moiety comprising a cleavable bond which is an amide —NHC(O)— or an ester —C(O)O— bond, or, alternatively, Y may be null, in which case the iodine-substituted group G is directly linked to the ester or amide functionality of the (meth)acrylate or (meth) acrylamido groups, respectively and wherein the iodine-substituted group G is a C3-C8 carbocyclic radical or aryl radical substituted by 2 to 5 iodine atoms, and wherein when m is 2 or 3, then G is optionally substituted by one or two substituents other than iodine.

16. Nanoparticles according to claim 15, wherein the monomer is represented by the following structure (4):

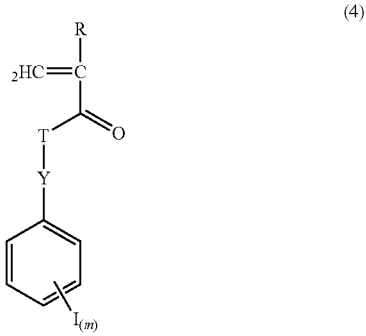

(4)

wherein R, T, Y are as defined in claim 15 and m is an integer in the range of 2 to 5, and wherein when m is 2 or 3, then the phenyl ring is optionally further substituted by one or two substituents other than iodine.

17. Nanoparticles according to claim 16, wherein the monomer is selected from the group consisting of 3-(methacryloylamido)-2,4,6-triiodobenzoic acid, 2-methacryloyloxyethyl (2,3,5-triiodobenzoate), -2,4,6-triiodophenyl-methacrylate and 2,4,6-triiodophenyl-acrylate.

18. Nanoparticles according to claim 13, wherein the polymer is a co-polymer which is the free-radical chain polymerization product of at least one iodine substituted vinyl monomer with at least one bi-functional monomer that contains, in addition to its polymerizable functionality, a second reactive chemical group.

19. A process, which comprises providing a vinyl monomer having at least one iodine-substituted side group, wherein said side group is bonded to said monomer by means of a cleavable bond, and polymerizing said monomer in the presence of a free radical initiator, to form nanoparticles having an average size of less than 2000 nm.

20. A process according to claim 19, carried out as emulsion polymerization.

21. A process according to claim 19, carried out as dispersion polymerization.

22. A process according to claim 19, wherein the vinyl monomer is represented by formula (4):

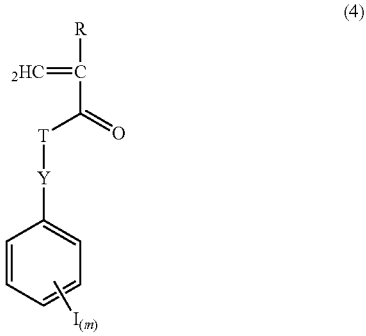

(4)

wherein R is H or methyl, T is O or NH, m is an integer between 2 and 5 and Y is a linking moiety comprising a cleavable bond which is an amide —NHC(O)— or an ester —C(O)O— bond, or, alternatively, Y may be null, in which case the iodine-substituted phenyl ring is directly linked to the ester or amide functionality of the (meth)acrylate or (meth) acrylamide groups, respectively and wherein when m is 2 or 3, then the iodine-substituted phenyl ring is optionally further substituted by one or two substituents other than iodine.

23. A process according to claim 22 wherein the monomer is selected from the group consisting of 3-(methacryloylamido)-2,4,6-triiodobenzoic acid, 2-methacryloyloxyethyl (2,3,5-triiodobenzoate), 2,4,6-triiodophenyl-methacrylate and 2,4,6-triiodophenyl-acrylate.

24. A process according to claim 19, wherein the average particle size of the resulting nanoparticles is in the range between 15 nm and 1000 nm.

25. A process according to claim 24, wherein the average particle size is in the range between 15 nm and 500 nm.

26. A process according to claim 19, wherein the vinyl monomer is polymerized on the surface of core particles, whereby the core particles are coated with one or more layers of the polymerization product.

27. A process according to claim 26, wherein the core of the particles comprises silica or a magnetic substance.

28. A process according to claim 19, wherein the iodine-substituted vinyl monomer is co-polymerized with a second monomer, said second monomer being a bi-functional monomer that contains, in addition to its polymerizable functionality, a second reactive chemical group.

29. A process according to claim 28, wherein the second monomer is glycidol methacrylate.

30. A process according to claim 19, which further comprises modifying the surface of the resulting nanoparticles by coating the same with an agent selected from the group consisting of surfactants, proteins and polysaccharides, to form surface-coated nanoparticles.

31. A process according to claim 19, which further comprises covalently binding to the surface of the nanoparticles or the coated nanoparticles a bi-functional polymer through the first functional group of said bi-functional substance, and subsequently optionally reacting the second functional group of said bi-functional substance with an homing agent selected from the group consisting of drugs, proteins, antigens and antibodies.

32. A radiographic composition comprising:
  X-ray contrast agent, which is the nanoparticles according to claim 1,
  a liquid carrier.

33. A radiographic composition according to claim 32 for use in diagnostic radiology, wherein the liquid carrier is a physiologically acceptable solution which optionally comprises a stabilizer.

* * * * *